US00PP33101P2

(12) United States Plant Patent
Horvath

(10) Patent No.: US PP33,101 P2
(45) Date of Patent: May 25, 2021

(54) ***BOUTELOUA GRACILIS* PLANT NAMED 'HONEYCOMB'**

(50) Latin Name: *Bouteloua gracilis*
Varietal Denomination: Honeycomb

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 16/974,245

(22) Filed: Dec. 1, 2020

(51) Int. Cl.
*A01H 6/46* (2018.01)
*A01H 5/12* (2018.01)

(52) U.S. Cl.
USPC ..... Plt./384

(58) Field of Classification Search
USPC ..... Plt./384
See application file for complete search history.

*Primary Examiner* — Annette H Para

(57) ABSTRACT

A new, distinct *Bouteloua gracilis* plant as shown and described, characterized by a height of 100 cm, and 199 B color inflorescence, compared to 45 cm height and RHS 145 A inflorescence of the parent plant.

1 Drawing Sheet

Figure 1:
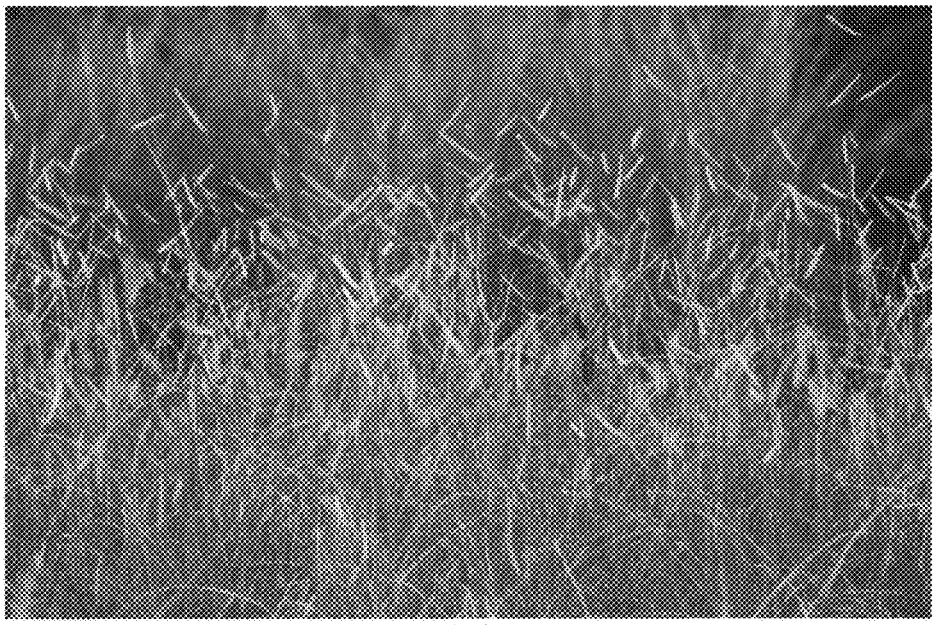

Latin name: *Bouteloua gracilis.*
Cultivar name: 'Honeycomb'.

BACKGROUND OF THE INVENTION

The present invention relates to a new form of *Bouteloua gracilis* plant named 'Honeycomb'. 'Honeycomb' is a seedling of *Bouteloua gracilis* plant named 'Blonde Ambition', U.S. Plant Pat. No. 22,048, characterized by a height of 100 cm, and 199 B color inflorescence, compared to 45 cm height and RHS 145 A inflorescence of the parent plant. The new plant was grown as a seedling of *Bouteloua gracilis* 'Blonde Ambition', U.S. Plant Pat. No. 22,048, by the inventor at a wholesale perennial nursery in Hebron, Ill. USA in 2017. The selection of this plant was due to its height of 100 cm, and 199 B color inflorescence. Asexual, vegetative division propagation has been the only means of reproduction. Propagation has taken place at the inventor's nursery in Hebron, Ill. since 2018. In 2019 we planted 500 plants in 1 gallon pots. To date these plants have remained uniform in height, and foliage color. The new *Bouteloua gracilis* has shown to be stable and identical in reproduction to the parent after making over 500 vegetative divisions from 2018 to 2020. No plants of the new *Bouteloua gracilis* have been sold in this country, or anywhere in the world, prior to the filing of this application, nor has any disclosure of the new plant been made prior to the filing of this application with the exception of that which was disclosed within one year of filing of this application and was either derived directly or indirectly from the inventor or his company in Hebron, Ill.

SUMMARY OF THE INVENTION

In the following description, color references are made to The Royal Horticultural Society Colour Chart (copyright 2001). The new *Bouteloua gracilis* plant named 'Honeycomb' has shown the following characteristics to be unique and stable. Height of 100 cm, and 199 B color inflorescence. For purpose of the comparison the new plant will be referred to as 'Honeycomb'.

Plants of 'Honeycomb' can be compared to plants of *Bouteloua gracilis* 'Blonde Ambition', U.S. Plant Pat. No. 24,048. 1. 'Honeycomb' has an upright growth and a height of 100 cm compared to the height of *Bouteloua gracilis* 'Blonde Ambition' which has a height of 45 cm. 2. 'Honeycomb' has inflorescence colored 199 B compared to *Bouteloua gracilis* 'Blonde Ambition' which has inflorescence colored 145 A.

Plants of 'Honeycomb' can be also be compared to plants of a *Bouteloua gracilis* seedling selection noted for its red inflorescence, not patented. 1. 'Honeycomb' has an upright growth and a height of 100 cm compared to the height of *Bouteloua gracilis* selection noted for its red inflorescence of 45 cm. 2. 'Honeycomb' has inflorescence colored 199 B compared to *Bouteloua gracilis* selection noted for its red inflorescence which has inflorescence colored red.

Plants of 'Honeycomb' can be also be compared to plants of a *Bouteloua gracilis* 'Bad River', not patented. 1. 'Honeycomb' has an upright growth and a height of 100 cm compared to the height of *Bouteloua gracilis* 'Bad River' which has a height of 45 cm. 2. 'Honeycomb' has inflorescence colored 199 B compared to *Bouteloua gracilis* 'Bad River' which has inflorescence colored tan to brown.

DESCRIPTION OF PHOTOGRAPHS

Figure 2:
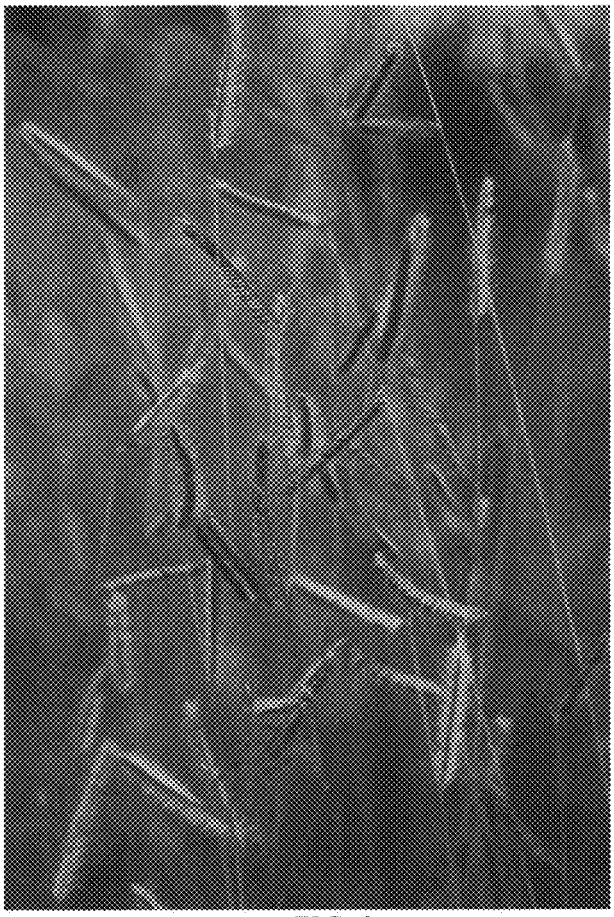

FIG. 1. Shows container plants blooming in July.
FIG. 2. Shows a close up of the flower in September.

DETAILED BOTANICAL DESCRIPTION

In the following description, color references are made to The Royal Horticultural Society Colour Chart. The plant herein described is an established 1 year old plant growing in a 3 gallon container, grown in full sun and irrigated in Hebron, Ill. USA. Measurements and numerical values represent averages of typical plants.

Botanical classification: *Bouteloua gracilis* plant named 'Honeycomb'.

Parentage: Female *Bouteloua gracilis* 'Blonde Ambition'. Male a *Bouteloua gracilis* seedling selection noted for its red flowers.

Propagation: Vegetative division.

Plant description: Overall habit of the new *Bouteloua gracilis* is clumping with upright culms topped by 199 B colored flowers beginning in July. Vigor is moderate.

*Plant height.*—100 cm.

*Plant width.*—70 cm.

Foliage and stems:

*Foliage description.*—Glabrous, flat blade, sheathed from node of attachment to ligule, linear.

*Type.*—Deciduous, grass growing in culms.

*Shape.*—Linear. Apex — Acute. Base — Truncate. Margin — Entire, flat. Arrangement — Alternate, basal.

*Ligules.*—Texture — ciliate. Length — 0.1 mm long. Color — 199 A.

*Number of blades.*—Typically 7 blades per stem.

*Blade length.*—1-2 mm wide, up to 17 cm long.

*Sheath.*—3 mm wide, ranging from 7 to 16 cm long.

*Adaxial leaf description.*—Leaf color is 146 A.

*Abaxial leaf description.*—Leaf color is 146 A.

*Culm description.*—Glabrous, erect, cylindrical.

*Culm or stem diameter.*—3 mm. Length — 80-100 cm. Color of the internodes is 147 B.

*Number of culms or stems per clump.*—150.

*Node description.*—Cylindrical.

*Number of nodes per culm.*—2-3, glabrous.

*Length of internodes.*—Ranges from 15-30, 25 cm average.

Flower inflorescence:

*Inflorescence type.*—Spike with sessile and pedicillate spikelets.

*Inflorescence color.*—As a whole the color is 199 A.

*Spikelet.*—2 mm wide, 5 cm long, color is 199 A.

*Arrangement.*—To one side of rachis.

*Panicle length.*—5 cm.

*Rachis length.*—5 cm.

*Palea.*—Awned, Keel- present. Pubescence — present.

*Glumes.*—Linear. 3-5 mm long, 1 mm wide. Lower glumes — 3 mm. Upper glumes — 5 mm. Pubescent on the nerve, otherwise glabrous.

*Lemma.*—3-awned.

*Flower number.*—Approximately 125 florets per rames, average 50 per spikelet.

*Androecium.*—Anthers — number 2, color — is yellow 11 A.

*Anther size.*—2 mm long by 1 mm wide.

*Fertility.*—Fertile with 2 Anthers and 1 Stamens.

*Bloom period and duration.*—Last two weeks of July to the end of September.

*Bloom color.*—199 A.

*Fruit or seeds.*—color is 199 A, size is 1-2 mm wide, 13 mm long.

*Scent.*—No scent.

*Roots.*—Fibrous, dense and freely branching.

*Fruit.*—199 A.

*Hardiness.*—United States Department of Agriculture Zones 4-9.

*Disease resistance.*—Plants are not susceptible to any major pests or diseases.

I claim:

1. A new, distinct *Bouteloua gracilis* plant as shown and described, characterized by a height of 100 cm, and 199 B color inflorescence, compared to 45 cm height and RHS 145 A inflorescence of the parent plant.

* * * * *